United States Patent [19]

Bencherif et al.

[11] Patent Number: 5,559,124

[45] Date of Patent: Sep. 24, 1996

[54] DEPOLARIZING SKELETAL MUSCLE RELAXANTS

[76] Inventors: Merouane Bencherif, 5437-B Countryside Dr., Winston-Salem, N.C. 27105; Patrick M. Lippiello, 1233 Arboretum Dr., Lewisville, N.C. 27023; William S. Caldwell, 1270 Yorkshire Rd., Winston-Salem, N.C. 27106

[21] Appl. No.: 462,421

[22] Filed: Jun. 5, 1995

Related U.S. Application Data

[62] Division of Ser. No. 301,288, Sep. 6, 1994, Pat. No. 5,510,355.

[51] Int. Cl.⁶ ..................................... A61K 31/44
[52] U.S. Cl. ........................................... 514/305
[58] Field of Search ............................... 514/305

[56] References Cited

U.S. PATENT DOCUMENTS

| | | | |
|---|---|---|---|
| 4,179,507 | 12/1979 | Stenlake et al. | 424/258 |
| 4,190,674 | 2/1980 | Grivsky | 424/324 |
| 4,508,715 | 4/1985 | Booth et al. | 514/280 |
| 4,701,460 | 10/1987 | El-Sayad et al. | 514/308 |
| 4,761,418 | 8/1988 | Swaringen, Jr. et al. | 514/308 |
| 4,923,898 | 5/1990 | Sunshine et al. | 514/557 |
| 5,015,741 | 5/1991 | Osdene et al. | 546/281 |
| 5,242,935 | 9/1993 | Lippiello et al. | 514/343 |
| 5,260,337 | 11/1993 | Sims et al. | 514/570 |
| 5,276,043 | 1/1994 | Lippiello et al. | 514/343 |

OTHER PUBLICATIONS

Sadikov et al., "Syntheses Based on Anabasine," pp. 3345–3347 (1962).

Rubtsov et al., "Hofmann Cleavage of 6, 9–Diazoniadispiro–(5.2.5.2) Hexadecane Dichloride with Methanolic Potassium Hydroxide," pp. 624–630 (1964).

Gilman et al., Goodman and Gilman's The Pharmacological Basis of Therapeutics, "Cholinergic Agonists," Chapter 5, pp. 91–99, Sixth Edition (1980).

Gilman et al., Goodman and Gilman's The Pharmacological Basis of Therapeutics, "Anticholinesterase Agents," Chapter 6, pp. 100–119, Sixth Edition (1980).

Gilman et al., Goodman and Gilman's The Pharmacological Basis of Therapeutics, "Neuromuscular Blocking Agents," Chapter 11, pp. 220–234, Sixth Edition (1980).

Physicians' Desk Reference, 48 Edition, pp. 689–691 (1994), "Anectine".

Physicians' Desk Reference, 48 Edition, pp. 758–760 (1994), "Tracrium Injection".

Physicians' Desk Reference, 48 Edition, pp. 1362–1363 (1994), "Paraflex".

Physicians' Desk Reference, 48 Edition, pp. 1648–1650 (1994), "Norcuron".

*Primary Examiner*—Marianne M. Cintins
*Assistant Examiner*—William R. A. Jarvis

[57] ABSTRACT

Compounds such as 2-acetoxymethylquinuclidine are useful as locally acting and highly selective muscle relaxants. Each compound, when administered intravenously, acts to bind to musculoskeletal nicotinic receptor sites in a reversible manner causing transient depolarization, and hence provides for reversible muscle relaxation to a patient during anesthesia.

8 Claims, No Drawings

DEPOLARIZING SKELETAL MUSCLE RELAXANTS

CROSS REFERENCE TO RELATED APPLICATION

This is a divisional of application Ser. No. 08/301,288, filed Sep. 6, 1994, now U.S. Pat. No. 5,510,355.

BACKGROUND OF THE INVENTION

The present invention relates to compounds having pharmaceutical properties, and in particular, to compounds having muscle relaxant properties. More specifically, the present invention relates to muscle relaxant compositions and to methods for providing muscle relaxation.

Various compounds having muscle relaxant properties are set forth in U.S. Pat. No. 4,190,674 to Grivsky; U.S. Pat. No. 4,508,715 to Booth et al; U.S. Pat. No. 4,7611,418 to Swaringen, Jr. et al; U.S. Pat. No. 4,701,460 to El-Sayad et al; U.S. Pat. No. 4,179,507 to Stenlake et al; U.S. Pat. No. 4,923,898 to Sunshine et al; U.S. Pat. No. 5,015,741 to Osdene et al and U.S. Pat. No. 5,260,337 to Sims et al.; as well as in Goodman and Gilman's *The Pharmacological Basis of Therapeutics*, Chapters 5 and 6, 6th Edit. (1980) and *Physicians Desk Reference*, 48 Edit., pp. 689, 758, 1362 and 1648 (1994).

Compounds having musculoskeletal relaxing properties include (1) agents acting in the central nervous system which are used to relieve pain associated with muscle contraction (e.g., 5-chlorobenzoxazolinone available as Parafon Forte DSC from McNeil Pharmaceutical), and (2) agents acting in the peripheral nervous system used primarily to induce muscle relaxation and hence reduce muscle contraction during anesthesia. The second group of muscle relaxants is subdivided into two groups: (i) non-depolarizing agents which inhibit the activation of muscle receptors (e.g., metocurarine iodide, d-tubocurarine, tubocurarine chloride, pancuronium, gallamine, diallytoiferine, toxiferine, atracurium besylate which is available as Tracrium from Burroughs-Wellcome Co., and vecuronium bromide which is available as Norcuron from Organon Inc.) and (ii) depolarizing agents which transiently activate muscle receptors and result in their blockade (e.g., decamethonium iodide, and succinylcholine chloride which is available as Anectine from Burroughs-Wellcome Co.). The effects of the depolarizing agents are manifested as fasciculations and flaccid paralysis which are observed to occur rapidly after their injection.

The effects of depolarizing agents (DA) and non-depolarizing agents (NDA) are separated based on their duration of action from ultrashort acting (e.g. for a depolarizing agent such as succinylcholine chloride) to intermediate (e.g. for a non-depolarizing agent such as atracurium besylate). Certain types of muscle relaxants are useful as neuromuscular blocking agents in clinical applications, and have found use as adjuvants to surgical anesthesia, in orthopedic surgical procedures and in facilitating endotracheal intubation procedures. Some of these compounds (e.g., succinylcholine chloride) are routinely used to provide muscle relaxation during cesarcan section procedures.

It is desirable for neuromuscular blocking agents to be locally acting and highly selective for binding to muscle nicotinic acetylcholine receptor sites. As such, when a patient is treated with anesthesia, the muscle relaxant is applied (e.g., intravenously or by injection), in order to cause the muscle to relax and hence minimize muscle contraction.

It would be desirable to provide a compound useful as a muscle relaxant. In particular, it would be desirable to provide an agonist which has activity at relatively low concentrations as a neuromuscular blocking agent. It would also be desirable to achieve muscle relaxation at concentrations of agonist that are devoid of any ganglionic effects (e.g., so as to not exhibit side effects such as those associated with interaction with cardiovascular sites). As such, it would be desirable to provide muscle relaxant compositions and methods for providing muscle relaxation.

SUMMARY OF THE INVENTION

In one aspect, the present invention relates to a method for providing relaxation of muscle. The method involves administering to a patient an effective amount of a pyridine compound substituted at its 3 position with a heterocyclic moiety incorporating nitrogen (i.e., a heterocyclic substituted pyridine) or a quinuclidine compound. Exemplary methods involve administering to a patient an effective amount of 5-chloronicotine, 5-fluoronornicotine, anabaseine, 5-fluoroanabaseine, 2-acetoxymethylquinuclidine or 2-(3-pyridyl)-quinuclidine.

The present invention, in another aspect, relates to a pharmaceutical composition comprising an effective amount of a heterocyclic substituted pyridine or a quinuclidine compound. Such a pharmaceutical composition has the capability of acting as a neuromuscular depolarizing agent, and hence has the capability of acting as a muscle relaxant. Exemplary pharmaceutical compositions acting as neuromuscular depolarizing muscle relaxants include as an active ingredient 5-chloronicotine, 5-fluoronornicotine, anabaseine, 5-fluoroanabaseine, 2-acetoxymethylquinuclidine or 2-(3 -pyridyl)-quinuclidine.

The pharmaceutical compositions of the present invention are beneficial as muscle relaxants in that the compositions have the potential to (i) act as a pharmacological tool to block transmission at the neuromuscular junction of a subject resulting in a general flaccid paralysis to the subject and (ii) provide a reversible relaxation of skeletal muscle. In addition, the compounds of the present invention are expected to have the potential to induce these effects at very low concentrations without any side effects associated with interactions at ganglionic-type receptor sites. The compounds of the present invention are locally acting and highly selective for binding to receptors within the muscle of a subject. The compounds of the present invention mimic the action of acetylcholine (i.e., a neurotransmitter) at nicotinic receptors, and hence act as depolarizing agents. However, the compounds do not act to any significant degree as substrates for acetylcholinesterase, and hence are not readily hydrolyzed or enzymatically degraded. However, the neuromuscular blocking activity of each of the compounds is reversible because of the ultimate degradation of those compounds (e.g., by hydrolysis caused by plasma and liver enzymes), in order that full recovery of muscle tone ultimately is achieved.

DETAILED DESCRIPTION OF THE PREFERRED EMBODIMENTS

The present invention, in one aspect, relates to the use of compounds having the general formula:

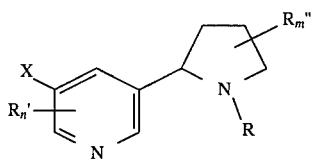

where R represents H or alkyl (e.g., lower alkyl containing 1 to 7 carbon atoms), preferably H or methyl; R' and R" individually represent a substituent other than hydrogen (e.g., alkyl, such as lower straight chain or branched alkyl, including alkyl moieties containing 1 to 7 carbon atoms); X, which is positioned at the 5 position of the pyridine ring, represents halo, such as F or Cl, or primary, secondary or tertiary amino, where the secondary and tertiary amino groups respectively include one or two alkyl substituents containing 1 to 6 carbon atoms; m is an integer which can range from 0–7, preferably 0 or 1; and n is an integer which can range from 0–3, preferably 0 or 1. However, the compound preferably is not substituted at the 2 and/or 4 positions of the pyridine ring, and if substitution of the pyridine ring occurs, that substitution most preferably is only at the 5 and/or 6 positions of the pyridine ring. As such, preferred compounds are 5-halo substituted nicotine or nornicotine compounds. Also of interest are 5-amino substituted nicotine and nornicotine compounds. Also of interest are 5-amino substituted nicotine and nornicotine compounds. Representative compounds are (+/−)-5-chloronicotine and (+/−)-5-fluoronornicotine. See, Rondahl, *Acta Pharm. Suec.*, Vol. 14 (2), p. 113 (1977).

The present invention, in another aspect, relates to the use of compounds having the general formula:

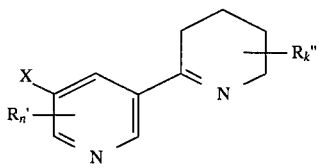

where R' and R" individually represent a substituent other than hydrogen (e.g., alkyl, such as lower straight chain or branched alkyl, including alkyl moieties containing 1 to 7 carbon atoms); X, which is positioned at the 5 position of the pyridine ring, represents a substitueat other than hydrogen (e.g., alkyl, such as lower straight chain or branched alkyl, including alkyl moieties containing 1 to 7 carbon atoms; or halo, such as F or Cl );or primary, secondary or tertiary amino, where the secondary and tertiary amino groups respectively include one or two alkyl substituents containing 1 to 6 carbon atoms; k is an integer which can range from 0–8, preferably 0 or 1; and n is an integer which can range from 0–3, preferably 0 or 1. However, the compound preferably is not substituted at the 2 and/or 4 positions of the pyridine ring, and if substitution of the pyridine ring occurs, that substitution most preferably is only at the 5 and/or 6 positions of the pyridine ring. As such, preferred compounds are 5-halo substituted compounds. Representative compounds are anabaseine and 5-fluoroanabaseine. See, Leete, *J.Org. Chem.*, Vol. 44, p. 165 (1979); Spath et al, *Chem. Ber.*, Vol. 69, p. 1082 (1936) and Kamimura et al, *Agric. Biol. Chem.*, Vol. 27, p. 450 (1963).

The present invention, in yet another aspect, relate to the use of compounds having the general formula:

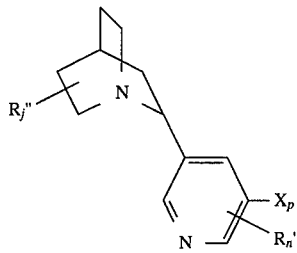

where R' and R" individually represent a substituent other than hydrogen (e.g., alkyl, such as lower straight chain or branched alkyl, including alkyl moieties containing 1 to 7 carbon atoms); X, which is positioned at the 5 position of the pyridine ring, represents a substiuent other than hydrogen (e.g., alkyl, such as lower straight chain or branched alkyl, including alkyl moieties containing 1 to 7 carbon atoms; or halo, such as F or Cl); or primary, secondary or tertiary amino, where the secondary and tertiary amino groups respectively include one or two alkyl substituents containing 1 to 6 carbon atoms; j is an integer which can range from 0–12, preferably 0 or 1; n is an integer which can range from 0–3, preferably 0 or 1; and p is an integer which is 0 or 1. However, the compound preferably is not substituted at the 2 and/or 4 position of the pyridine ring, and if substitution of the pyridine ring occurs, that substitution most preferably is only at the 5 and/or 6 positions of the pyridine ring. One preferred compound is (+/−)-2-(3-pyridyl)-quinuclidine, for which n is 0, j is 0 and p is 0.

The present invention, in yet another aspect, relates to the use of compounds having the general formula:

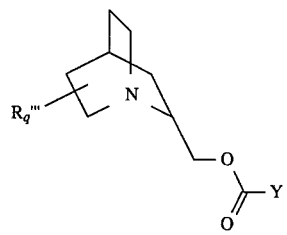

where R''' represents a substituent other than hydrogen (e.g., alkyl, such as lower straight chain or branched alkyl, including alkyl moieties containing 1 to 7 carbon atoms; or halo, such as F or Cl); Y is a lower straight chain or branched alkyl or substituted straight chain or branched alkyl, such as alkyl moieties containing 1 to 7 carbon atoms (e.g., methyl or ethyl); and q is an integer which can range from 0–12, preferably 0 or 1. One preferred compound is (+/−)-2-acetoxymethylquinuclidine, for which q is 0, and Y is methyl.

The present invention relates to a method for treating a patient during surgical procedures requiring anesthesia and musculoskeletal relaxation. In particular, the method comprises administering to the patient an amount of a compound effective for providing relaxation of muscle. The method involves administering an effective amount of a compound selected from the general formulae which are set forth hereinbefore. The present invention relates to a pharmaceutical composition incorporating a compound selected from the general formulae which are set forth hereinbefore. These compounds can be employed as racemic mixtures or as enantiomers. Those compounds can be employed in salt form (e.g., as chloride, perchlorate, picrate, sulfate, tartrate, fumarate, citrate, malate, lactate or aspartate salts).

The manner in which the compounds are administered can vary. Although it is possible to administer the compound in the form of a bulk active chemical, it is preferred to present the compound in the form of a pharmaceutical composition or formulation for parenteral administration. As such, a preferred pharmaceutical composition includes the compound as an active ingredient, and a pharmaceutically acceptable carrier. Typically, the pharmaceutical composition is administered as an aqueous or non-aqueous solution, as a suspension, or as an emulsion in a pharmaceutically acceptable liquid or mixture of liquids. The compound within the pharmaceutical composition is administered internally by injection or intravenously. For example, the pharmaceutical composition can be administered intravenously as an infusion (e.g., within aqueous dextrose or saline solutions). Exemplary methods for administering such muscle relaxant compounds (e.g., so as to achieve sterile or aseptic conditions) will be apparent to the skilled artisan. Certain methods suitable for administering compounds useful according to the present invention are set forth in Goodman and Gilman's *The Pharmacological Basis of Therapeutics*, 6th Edit. (1980). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anethesia is administered. The frequency of administration normally is determined by an anesthesiologist, and typically varies from patient to patient.

The pharmaceutical composition also can include various other components as additives or adjuncts. Exemplary pharmaceutically acceptable components or adjuncts include anesthetics, anti-oxidants, bacteriostatic agents, buffering agents, analgesics, anti-inflammatory agents, anti-pyretics, thickening agents and suspending agents. Such components can provide additional therapeutic benefit, or act towards preventing any potential side effects which may be posed as a result of administration of the pharmaceutical composition.

The dose of the compound is that amount effective to provide a desired effect for a desired time frame. By "effective amount" or "effective dose" is meant that amount parenterally administered (e.g., injected intravenously) sufficient to bind to relevant receptor sites on the musculoskeletal fiber of the patient, and to elicit neuropharmacological effects (e.g., elicit brief depolarization, thus resulting in effective short duration relaxation of skeletal muscle). Short duration typically ranges from about 5 to about 60 minutes. As such, the compounds have the ability to act as nicotinic depolarizing agents, and neuromuscular paralysis is induced by administering an effective amount of compound.

An effective amount of the compound administered to a patient provides rapid onset and short-lived muscle relaxation. For adult human patients undergoing short surgical procedures, the effective dose of typical compounds injected intravenously generally is at least about about 0.001 mg/kg patient weight; but generally does not exceed about 0.5 mg/kg patient weight, often does not exceed about 0.1 mg/kg patient weight, and frequently does not exceed about 0.05 mg/kg patient weight. Following administration of typical compounds in such a concentration range, the onset of paralysis normally develops within 1 to 2 minutes, and is reversible (i.e., muscle tone returns within a short period of time). For adult human patients undergoing long surgical procedures, the effective dose of typical compounds is administered through continuous or intermittent intravenous perfusion at a rate which is at least about 0.001 mg/minute; but generally does not exceed about 0.5 mg/minute, often does not exceed about 0.1 mg/min., and frequently does not exceed about 0.05 mg/min. Following administration of typical compounds in the specified amounts, the onset of paralysis typically develops within 1 to 2 minutes and persists for the duration of the superfusion.

For human patients in the pediatric population undergoing short surgical procedures, the effective dose of typical compounds injected intravenously generally is at least about about 0.001 mg/kg patient weight; but generally does not exceed about 0.2 mg/kg patient weight, often does not exceed about 0.1 mg/kg patient weight, and frequently does not exceed about 0.05 mg/ kg patient weight. Following administration of typical compounds in such a concentration range, the onset of paralysis normally develops within 1 to 2 minutes, and persists for a short period of time before recovery is achieved. For infants and children undergoing long surgical procedures, the effective dose of typical compounds is administered through continuous or intermittent intravenous perfusion at a rate which is at least about 0.001 mg/ minute; but generally does not exceed about 0.2 mg/ minute, often does not exceed about 0.1 mg/ min., and frequently does not exceed about 0.05 mg/min. The total amount of drug administered using such a parenteral route of administration generally does not exceed a total of 10 mg, often does not exceed 5 mg and frequently does not exceed 2 mg. Following administration of typical compounds in the specified amounts, the onset of paralysis typically develops within 1 to 2 minutes and persists for the duration of the superfusion.

The compounds useful according to the method of the present invention have the ability to bind to, and cause transient activation of the nicotinic receptor on the musculoskeletal fiber, and hence cause reversible muscle relaxation. As such, the compounds have the ability to act as depolarizing skeletal muscle blockers. Those compounds are very potent active ingredients of muscle relaxant compositions. Compounds of the present invention can be more than about 10 times, often more than about 20 times, frequently more than about 100 times, and even more than about 500 times, more potent than an equal amount of similarly administered succinylcholine chloride, with regards to causing muscle relaxation. That is, typical compounds useful in carrying out the present invention provide for depolarization block in amounts generally 10 times less, often 20 times less, frequently 100 times less, and even 500 times less than the amount of succinylcholine necessary to achieve similar effects.

The compounds useful according to the method of the present invention have the ability to demonstrate activation of human muscle receptors as is evidenced by their ability to effectively elicit isotopic ion flux as measured using an assay sensitive to a nicotinic receptor agonist. As such, such compounds have the ability to cause activation, depolarization and neurormuscular blockade leading to flaccid paralysis. The parameters for receptor activation used in the present invention provide a measure of the concentration needed to achieve 50% of the maximal activation of the receptors (EC50). The receptor activation constants of typical compounds useful in carrying out the present invention generally are greater than 1 nM, often are greater than 50 nM, and frequently are greater than about 100 nM. The receptor activation constants of such typical compounds generally are less than 10 µM, often are less than about 1 µM, frequently are less than about 500 nM, and even are less than about 100 nM. Receptor activation constants provide a measure of the concentration of the compound needed to activate half of the relevant receptor sites of the skeletal muscle of a patient. See, Goodman and Gilman's *The Pharmacological Basis of Therapeutics*, 6th Edit. (1980).

The compounds of the present invention are very effective muscle relaxants. Typical compounds useful in carrying out the present invention induce effects reaching maximal values generally in excess of 130%, often in excess of 100% and frequently in excess of 80% of that reached by succinylcholine. Compounds useful in carrying out the present invention can induce effects reaching maximal values in excess of 200% of that reached by succinylcholine.

The compounds of the present invention, when employed in effective amounts in accordance with the method of the present invention, are selective to muscle nicotinic receptor sites and result in no significant or detectable activation of ganglion-type receptors. By this is meant that a particular dose of compound resulting in full activation of muscle receptors thereby causing depolarization block is essentially completely ineffective in eliciting activation of ganglionic-type receptors. As such, administration of compounds of the present invention provides a therapeutic window in which muscle relaxation is induced, and side effects associated with ganglionic-type receptor activation are avoided. That is, an effective dose of the compound of the present invention is sufficient to provide muscle relaxation by causing depolarization of muscle receptors, but is insufficient (i.e., is not at a high enough level) to provide activation of ganglionic-type receptors and hence cause undesirable side effects. Typically, activation of nicotinic muscle receptors by compounds of the present invention occurs upon application of amounts less than about 1/10, and often less than about 1/20, of those amounts sufficient to cause activation of ganglionic-type receptors.

The compounds useful according to the method of the present invention lack the ability to activate nicotinic function of adrenal chromaffin tissue. Such a tissue has a high concentration of ganglionic-type receptors relative to muscle receptors. This is evidenced as the compounds of the present invention exhibit poor ability to activate isotopic rubidium ion flux through nicotinic receptors in cell preparations derived from adrenal gland. Generally, typical compounds useful in carrying out the present invention activate isotopic rubidium ion flux through receptors by less than 10 percent, often by less than 5 percent, and frequently by less than 2 percent of that elicited by an equal molar amount of a nicotinic agonist such as acetylcholine or carbachol.

The following example is provided in order to further illustrate various embodiments of the invention but should not be construed as limiting the scope thereof. Unless otherwise noted, all pans and percentages are by weight.

EXAMPLE 1

Sample No. 1 is (+/−)-2-(3-pyridyl)-quinuclidine difumarate, which was prepared essentially in accordance with the following techniques.

N-(diphenylmethylene)-3-(aminomethyl) pyridine (I): Benzophenone (10.92 g, 60 mmol), 3-(aminomethyl)-pyridine (6.48 g, 60 mmol) and p-toluene sulfonic acid (10 mg) were dissolved in 30 mL benzene, heated to reflux under a nitrogen atmosphere with a Dean-Stark trap. The completion of the reaction (12–16 hours) was determined after the calculated amount of water was collected in the Dean-Stark trap. Benzene was removed on a rotary evaporator and Schiff base (I) obtained was used without any further purification.

Diethyl tetrahydropyran-4,4-dicarboxylate (II): Sodium (6.9 g, 0.3 mole) was dissolved in dry ethanol (100 mL), followed by addition of diethyl malonate (48.0 g, 0.3 mole) and chloroethyl ether (21.4 g, 0.15 mole). The reaction mixture was refluxed under a nitrogen atmosphere for 16 hours, cooled to room temperature followed by removal of ethanol on a rotary evaporator. HCl (10% aq., 25 mL) was then added to dissolve the residue. The aqueous solution was extracted with ethyl acetate (3×25 mL). Drying of the combined organic extracts over magnesium sulfate, and filtration followed by removal of ethyl acetate on a rotary evaporator yielded 55 g of pale yellow oil. Distillation was carried out at 25 mm of Hg and the fraction boiling at 166°–185° C. was collected to obtain 20.1 g (59% yield) of (II) as a colorless oil which was more than 85% pure.

Tetrahydropyran-4-carboxyllic acid (III): Diethyl tetrahydropyran-4,4-dicarboxylate (II) (5.00 g, 21.72 mmol) was added to a round bottom flask containing KOH (2.70 g, 48.12 mmol) dissolved in absolute ethanol (21 mL). The reaction mixture was heated to reflux for 6 hours, cooled to room temperature and water (15 mL) was added to the white suspension. Ethanol was removed on a rotary evaporator followed by addition of water (25 mL) and sulfuric acid (enough to make the solution acidic) to the residue. The acidic solution was then extracted with ether (10×30 mL) and the combined organic extracts were dried over magnesium sulfate. Filtration, followed by evaporation of ether yielded 3.84 g of a white solid, which was crushed to a fine power and washed three times with hexane. The solid was then heated at 180° C. for 1 hour to obtain 2.6 g (92% yield) of tetrahydropyran-4-carboxyllic acid (III) as a white solid. A small sample was crystallized from ethyl methyl ketone, m.p. 86°–88° C.

Tetrahydropyran-4-methanol (IV): To a suspension of tetrahydropyran-4-carboxyllic acid (III) (1.28 g, 10 mmol) in dry tetrahydrofuran (THF) (20mL), lithium aluminum hydride (1.14 g, 30 mmol) was added in small portions. The reagents were heated to reflux under a nitrogen atmosphere for 16 hours and then cooled to 0° C. Reaction was then quenched by adding water (1.14 mL,), and NaOH (15% aq., 1.14 mL) followed by stirring for 15 minutes and finally addition of water (3.42 mL). The salts formed were removed by filtration and the THF solution was dried over anhydrous potassium carbonate. Filtration, followed by rotary evaporation of THF yielded alcohol (IV) as a thick, colorless oil (1.0 1 g, 87% yield) which was used in the next step without any further purification.

Tetrahydropyran-4-methanol methanesulfonate (V): To a solution of (IV) (1.25 g, 10.78 mmol) in dry THF (20 mL) at 0° C. under a nitrogen atmosphere was added triethyl amine (2.26 mL, 16.17 mmol) followed by methanesulfonyl chloride (1.0 mL, 12.94 mmol). The ice bath was removed and the reaction mixture was stirred for an additional 2 hours. Sodium bicarbonate (10% aq., 20 mL) was then added to the reaction mixture followed by extraction with ethyl acetate (3×20 mL). Combined organic extracts were then dried over anhydrous potassium carbonate. Filtration, followed by evaporation of solvents on a rotary evaporator yielded the mesylate (V) as a yellow oil (2.01 g, 96% yield).

1-Amino-1-(3-pyridyl)-2-(4-tetrahydropyran)-ethane (VI): LDA (10 mmol) was generated at 0° C. by adding n-BuLi (4.17 mL of 2.4M solution, 10 mmol) to a solution of diisopropyl amine (1.53 mL, 10.91 mmol) in dry THF (10 mL). (I) (2.47 g, 9.09 mmol) was dissolved in dry THF (10mL) and cooled to −78° C. under a nitrogen atmosphere. LDA was then transferred to the solution of I using a double tipped needle under the pressure of nitrogen. The purple suspension was stirred for another 45 minutes during which time the temperature of the reaction mixture was allowed to rise to −45° C. Mesylate (V) in THF (5 mL) was then added via a syringe and the reaction mixture was allowed to reach room temperature, followed by additional stirring for 12 hours. HCl (10% aq., 20 mL) was added to the reaction mixture and stirred for 20–30 minutes followed by extraction with ethyl acetate (3×25 mL). The aqueous solution was first made basic by adding solid potassium carbonate and then extracted with chloroform (3×25 mL). Combined organic extracts were dried over potassium carbonate. Filtration, followed by evaporation of chloroform yielded compound (VI) as a brown oil (1.41 g, 75%).

(+/−)-2-(3-Pyridyl)-quinuclidine (VII): Amine (VI) (1.03 g, 5 mmol) was dissolved in HBr (aq., 48%, 12 mL). HBr gas was generated (according to the procedure described in Vogel's Textbook of Practical Organic Chemistry, Longman Scientific & Technical, 5th Ed., p. 437) by drop-wise addition of bromine to tetralene and then passed through the acidic solution of amine (VI) to make the solution saturated with HBr. The solution was then carefully transferred to a pressure tube and heated at 100° C. under pressure for 12–16 hours. The reaction mixture was allowed to cool down to room temperature and then transferred to a round bottom flask. Basification with solid potassium carbonate was followed by heating the reaction mixture at 80° C. for 24 hours. After cooling to room temperature the reaction mixture was extracted with chloroform (3×15 mL). Combined organic extracts were dried over potassium carbonate. Filtration, followed by removal of solvent on a rotary evaporator yielded 84 mg of a dark brown oil which was purified by silica gel column chromatography using 15% methanol in chloroform as the eluting solvent to obtain (VII) as a pale brown oil. Further purification was achieved by distillation (137°–138° C. at 0.3 mm Hg) to obtain (+/−)-2-( 3-pyridyl)-quinuclidine (VII) as a colorless oil (39 mg, 4.1% yield). The difumarate salt of (VII) was made by dissolving (VII) in ethanol (2 mL) and refluxing with fumaric acid (48 mg, 0.41 mmol). Removal of ethanol yielded the difumarate, m.p. 168°–171° C.

Sample No. 2 is 5-fluoroanabaseine dipicrate, which was prepared essentially in accordance with the techniques described in Leete, *J. Org. Chem.*, Vol. 44, p. 165 (1979).

Sample No. 3 is anabaseine dihydrochloride, which was prepared essentially in accordance with those techniques described in Spath et al, *Chem. Ber.*, Vol. 69, p. 1082 (1936) and Kamimura et al, *Agric. Biol. Chem.*, Vol. 27, p. 450 (1963).

Sample No. 4 is (+/−)-2-acetoxymethylquinuclidine perchlorate, which was prepared essentially in accordance with the following techniques.

Hydrochloride salt of 3-(4-pyridyl)-2-carboethoxy propenoic acid ethyl ester (II): Diethyl malonate (100 mmol, 16.0 g), pyridine-4-carboxaldehyde (100 mmol, 9.54 mL) and piperidine (0.2 mL) were dissolved in benzene (30mL) in a 200 mL flask fitted with a condenser and a Dean-Stark trap. The reaction mixture was refluxed for 24 hours when about 2.1 mL water was collected in the trap. Benzene and piperidine were removed on a rotary evaporator to obtain a pale yellow oil (I) (27.2 g) which was converted to its hydrochloride salt as follows: Ethanol (125 mL) was cooled to 5° C. using an ice-water bath followed by dropwise addition of acetyl chloride (15 mL). To the resulting solution was added a solution of (I) in diethyl ether (125 mL) until the pH of the resulting solution became 3–4. The contents were mixed with diethyl ether (200 mL). Filtration followed by drying under high vacuum yielded (II) as a yellow solid (31.2 g) which was used without further purification.

Hydrochloride salt of 3-(4-piperidyl)-2-carboethoxy propenoic acid ethyl ester (III): The mixture of (II) (30.0 g) in ethanol (50 mL, 60% aqueous) and platinum oxide (330 mg) was hydrogenated in a Parr apparatus at 60 psi for 16 hours. Filtration through celite followed by removal of solvents on a rotary evaporator yielded (III) as a yellow solid which was dried under vacuum at ambient temperature.

Hydrobromide salt of 3-(4-piperidyl)-2-bromo-2-carboethoxy propanoic acid ethyl ester (IV): A solution of bromine (0.07 mmol, 3.5 mL) in chloroform (90 mL) was added dropwise to a solution of (III) (0.07 mmol, 20.65) in dry chloroform (90 mL) under a nitrogen atmosphere and the solution was stirred for an additional 16 hours. Removal of chloroform on a rotary evaporator yielded (IV) as a yellow solid (45 g).

2,2-dicarboethoxy quinuclidine (V): (IV) (10 g) was suspended in water (50 mL) followed by addition of potassium carbonate until the solution was basic to pH paper. Additional potassium carbonate (2.0 g) was added and the suspension was heated to 55° C. for 1 hour. After cooling, the oil layer that formed was extracted with diethyl ether (3×30 mL). The combined organic extracts were dried over potassium carbonate and concentrated on a rotary evaporator to yield (V) as a pale brown oil (5.88 g).

Hydrochloride salt of racemic 2-quinuclidine carboxylic acid (VI): Concentrated HCl (50 mL) was added to a flask containing (V) (5.0 g) and the reagents refluxed for 12 hours. After cooling to room temperature, HCl was removed on a rotary evaporator to obtain (VI) as a brown solid in quantitative yield, which was dried by adding benzene (3×20 mL) and then concentrated on a rotary evaporator, followed by drying under vacuum at room temperature. M.p. is 294°–298° C.

Racemic 2-(hydroxymethyl)-quinuclidine (VII): Lithium aluminum hydride (0.1 mol, 3.9 g) was suspended in THF (200mL) in a 50 mL flask at 0° C. (VI) (0.03 mol, 5.76g) was added in small portions. After the addition, the reagents were refluxed under a nitrogen atmosphere for 12 hours, cooled to 0° C. followed by dropwise addition of water (3.8 mL) and NaOH (3.9 mL of a 15% aqueous solution). After stirring for 30 minutes, water (12 mL) was added to the reaction mixture followed by additional stirring for 30 minutes. The reaction mixture was filtered, and hot THF was used for additional washings of the precipitate. The filtrate obtained was dried over anhydrous potassium carbonate and filtered again. Removal of THF on a rotary evaporator yielded (VII) as a colorless oil (5.1 g). Distillation at 0.3 mm Hg yielded (VII) (2.75 g) as a clear oil.

Racemic 2-(acetoxymethyl)-quinuclidine (VIII): Acetic anhydride (45 mmol, 4.59 g) was added to a solution of (VII) in dry pyridine (40 mL) and the reagents refluxed under nitrogen for 24 hours. The reaction mixture was cooled to room temperature, and pyridine and excess acetic anhydride were removed along with added toluene using a rotary evaporator. The brown oil thus obtained was taken in a saturated solution of sodium bicarbonate (30 mL) followed by extraction with chloroform (3×25 mL). Combined organic extracts were dried over anhydrous potassium carbonate. Filtration followed by concentration on a rotary evaporator yielded a brown oil (2.64 g) which was distilled (90°–94° C. at 0.35 mm Hg) to obtain (VIII) as a colorless oil (2.25 g). Perchloric acid (1.00 g) was added to (VIII) in ethanol (10 mL). Removal of ethanol on a rotary evaporator followed by recrystallization in ethanol yielded the perchlorate salt of (VIII) (2.5 g) which was dried under vacuum at 130° C.

Sample No. 5 is (+/−)-5-fluoronornicotine, which was prepared essentially in accordance with the following techniques.

N-benzyl-5-bromopseudooxynicotine (I): To N-benzylpyrrolidone (10.54 g, 0.06 mol) in dry THF (60 mL) contained in a 250 mL flask under a nitrogen atmosphere was added NaH (60%, 2.26 g, 0.06 mol), and the mixture was heated under nitrogen for 30 min at 60° C., during which time the reaction became exothermic with evolution of hydrogen gas. After cooling to ambient temperature, ethyl-5-bromonicotinate (10 g, 0.043 mol) dissolved in dry THF (25 mL) was added dropwise, and the mixture refluxed overnight under nitrogen, during which time a solid mass appeared in the flask. After cooling to ambient temperature, the mixture was poured into ice-water (50 mL) and the pH of the resulting solution adjusted to 8–9 with aqueous HCl. The mixture then was extracted with chloroform (4×50 mL), the combined chlorform extracts dried over anhydrous potassium carbonate, and filtered and concentrated to give a brown solid (14.5 g) which was used without further purification. The brown solid material was mixed with concentrated HCl (50 mL) and the mixture refluxed overnight. The excess aqueous HCl was removed on a rotary evaporator and the resulting residue crystallized from absolute ethanol to afford (I) (9.5 g, 84%), m.p. 134°–135° C., as a light brown solid.

N-benzyl-5-bromonornicotine (II): (I) (9 g, 0.021 mol) was dissolved in methanolic KOH (10 % w/v, 75 mL) and the pH of the solution adjusted to 8–9. Sodium borohydride (2.8 g, 0.068 mol) was added over a period of 30 min, and the mixture was stirred for 3 hr at ambient temperature. The methanol was removed on a rotary evaporator and the residue was dissolved in water (25 mL) and the resulting solution extracted with chloroform (25 mL×3). The combined chloroform extracts were dried over anhydrous potassium carbonate, filtered and evaporated to low volume. Chromatography on silica gel (200–400 mesh) with chloroform/methanol eluant afforded (II) which was crystallized from absolute ethanol to afford a cream-colored solid (6.1 g, 83%), m.p. 73°–74° C. The reaction product was purified by vacuum distillation to afford a colorless oil, b.p. 172°–175° C. at 0.03 mm Hg, which solidified soon after collection.

5-amino-N-benzylnornicotine (IID: (II) (6.0 g, 0.019 mol), copper sulfate (2.0 g) and aqueous ammonium hydroxide (28% w/v, 50 mL) were placed in a stainless steel reaction bomb, and the bomb was sealed and heated to 200°–220° C. for 48 hr. The bomb was cooled and the aqueous reaction mixture extracted with chloroform (4×50 mL). The combined chloroform extracts were dried over anhydrous potassium carbonate, filtered, concentrated on a rotary evaporator and chromatographed on silica gel (200–400 mesh) with chloroform/methanol (98:2) as eluant to afford (III) (4.1 g, 87%) m.p. 127°–129° C. as a cream-colored powder.

N-benzyl-5-fluoronornicotine (IV): (III) (4.0 g, 0.016 mol) was dissolved in ethanol (4 mL). Fluoroboric acid (8 mL, 50% solution in water) was added, and the mixture was stirred for 10 min. The temperature Of the reaction was lowered to 0 to −5° C., and isoamylnitrite (4 mL, 97%, 0.379 mol) was added. After stirring, the reaction mixture at −5° C. to +5° C. for 30 minutes, diethyl ether (10 mL) was added and the stirring continued for 30 minutes. The reaction flask then was immersed in a dry ice/acetone mixture, and the precipitated solids filtered off. The filtered solid was washed with very cold ethanol and petroleum ether. The resulting precipitate (about 6 g) was transferred to a 100 mL flask. Dry benzene (50 mL) was added and the mixture refluxed for 3–4 hr. until the solid became and oil that was immiscible with benzene. The solvent was then removed on a rotary evaporator, aqueous HCl (6N, 5 mL) added and the solution refluxed for 4 hr. On cooling to ambient temperature, the pH of the solution was adjusted to 8–9 with NaOH solution, and extracted with chloroform (25 mL×3). The combined chloroform extracts were dried over anhydrous potassium carbonate, filtered, concentrated on a rotary evaporator and chromatogmphed on silica gel (200–400 mesh) with chloroform/methanol (98:2) as eluant to afford (IV) (3.2 g, 80%) as a yellow oil.

5-fluoronornicotine (V): (IV) (4.0 g, 0.015 mol) was dissolved in methanol (25 mL) and methanolic formic acid (44% w/v, 25 mL) added to the mixture. The mixture was stirred under a nitrogen atmosphere over Pd-C (5%, 100 mg) for 45 min. The reaction mixture was filtered, the solvent evaporated to dryness, and the residue dissolved in water (10 mL). The pH of the resulting solution was adjusted to 8–9 with aqueous NaOH, and the solution extracted with chloroform (3×10 mL). The combined chloroform extracts were dried over anhydrous sodium carbonate, filtered, concentrated and the oily residue distilled to afford (+/−)-5-fluoronornicotine (V) as a colorless liquid (2.3 g, 87%) b.p. 71° C.; 0.03 mm Hg.

Sample No. 6 is (+/−)-5-chloronicotine perchlorate, which was prepared essentially in accordance with the techniques described in Rondahi, *Acta. Pharm. Suec.*, Vol. 14 (2), p. 113 (1977).

For comparison purposes, Sample Nos. C-1 and C-2 are provided. These samples include acetylcholine (a naturally occurring neurotransmitter) and succinylcholine chloride (a known muscle relaxant), respectively.

The selectivity at muscle nicotinic receptors of the various analogs described in this invention was determined by their functional efficacies and potencies at muscle and ganglionic sites.

Human muscle activation was established on the human clonal line TE671/RD which is derived from an embryonal rhabdomyosarcoma (Stratton et al., *Carcinogen,* Vol. 10, pp. 899–905 (1989)). As evidenced through pharmacological (Lukas, *J. Pharmacol. Exp. Ther.,* Vol. 251, pp. 175–182 (1989)), electrophysiological (Oswald et al, *Neurosci. Lett.,* Vol. 96, pp. 207–212 (1989)), and molecular biological studies (Luther et al., *J. Neurosci.,* Vol. 9, pp. 1082–1096 (1989)) these cells express muscle-like nicotinic receptors.

Ganglionic effects were established on the rat pheochromocytoma clonal line PC 12 which is a continuous clonal cell line of neural crest origin derived from a tumor of the rat adrenal medulla expressing ganglionic-type neuronal nicotinic receptors. See, Whiting et al., *Nature*, Vol. 327, pp. 515-518 (1987); Lukas, *J. Pharmacol. Exp. Ther.*, Vol. 251, pp. 175-182 (1989); Whiting et al *Mol. Brain Res.*, Vol. 10, pp. 61-70 (1990). Discussion concerning the heterogeneity of nicotinic receptors subtypes is set forth in Lukas et al., *Internatl. Review Neurobiol.*, Vol. 34, pp. 25-130 (1992). Acetylcholine nicotinic receptors expressed in rat ganglia share a very high degree of homology with their human counterparts. See, Fornasari et al., *Neurosci. Lett.*, Vol. 111, pp. 351-356 (1990) and Chini et al., *Proc. Natl. Acad. Sci. USA*, Vol. 89, pp. 1572-1576 (1992).

Both clonal cell lines described above were maintained in proliferative growth phase according to routine protocols (Bencherif et al., *Mol. Cell. Neurosci.*, Vol. 2, pp. 52-65, (1991) and Bencherif et al., *J. Pharmacol. Exp. Ther.*, Vol. 257, pp. 946-953 (1991)). Intact cells on dishes were used for functional studies. Routinely, sample aliquots were reserved for determination of protein concentration using the method of Bradford, *Anal. Biochem.*, Vol. 72, pp. 248-254 (1976) with bovine serum albumin as the standard.

Nicotinic acetylcholine receptor (nAChR) function was assayed using $^{86}Rb^+$ efflux according to a method described by Lukas et al., *Anal. Biochem.*, Vol. 175, pp. 212-218 (1988). Cells were plated in 35-mm diameter wells of 6-well dishes for at least 48 hours and loaded for at least 4 hours at 37° C. in a medium containing serum, and 1 µCi/ml $^{86}Rb^+$. Following removal of the loading medium, cells were quickly washed three times with label-free Ringer's solution and exposed for 4 minutes at 20° C. to 900 µl of Ringer's containing the indicated concentration of compound to be tested (to define total efflux) or in addition to 100 µM mecamylamine (to define non-specific efflux). The medium was removed and $^{86}Rb+$ was quantitated using Cerenkov detection. See, Lukas et al., *Anal. Biochem.*, Vol. 175, pp. 212-218 (1988). Specific ion efflux was determined as the difference in isotope efflux between total and non-specific efflux samples. Dose-response curves were plotted and the concentration resulting in half maximal activation of specific ion flux through nicotinic receptors determined for human muscle and rat ganglionic preparations (EC50). The maximal activation for individual compounds was determined as a percentage of the maximal activation induced by acetylcholine, the endogenous neurotransmitter at muscle and ganglionic sites (Emax).

Data are presented in Table I.

TABLE I

| Sample | HUMAN EC50 (nM) | MUSCLE Emax (%) | RAT EC50 (nM) | GANGLIA Emax (%) |
|---|---|---|---|---|
| 1 | 55 | 130 | 2000 | 100 |
| 2 | 1000 | 220 | * | 0 |
| 3 | 2000 | 200 | 50000 | 80 |
| 4 | 3000 | 200 | 50000 | 60 |
| 5 | 30000 | 160 | ** | <10 |
| 6 | 30000 | 110 | * | 0 |
| C-1*** | 7000 | 100 | 40000 | 100 |
| C-2*** | 30000 | 95 | * | 0 |

TABLE I-continued

| Sample | HUMAN EC50 (nM) | MUSCLE Emax (%) | RAT EC50 (nM) | GANGLIA Emax (%) |
|---|---|---|---|---|

*Not applicable due to lack of activation
**Not applicable due to very low activation
***Not an example of the invention The data in Table I indicate the concentrations at which the various compounds activate human muscle receptor and ganglionic-type receptors (EC50 expressed in nanomolar concentrations), and the extent of such activation (Emax expressed as percentage of the effect induced by the endogenous neurotransmitter, acetylcholine). The data indicate that compounds of the present invention have the capability to activate human muscle receptors without activating ganglionic-type nicotinic acetylcholine receptors to any significant degree. For comparison purposes, data are provided for samples incorporating acetylcholine (i.e., an endogenous neurotransmitter) which has a tendency to be hydrolyzed rapidly by enzymes present within the subject; and succinylcholine (i.e., a known depolarizing muscle relaxant). Sample No. 2 is very potent relative to succinylcholine (Sample No. C-2) as evidenced by the respective EC50 values, is very efficacious relative to succinylcholine as evidenced by the respective Emax values, and causes no observed ganglionic effects. Sample Nos. 1, 3 and 4 are more potent and more efficacious than succinylcholine; however, these compounds exert effects at ganglionic-type receptors only at relatively high concentrations, thereby providing a significant therapeutic window for use of these compounds as muscle relaxants. Sample Nos. 5 and 6 are at least as potent as succinylcholine, and are more efficacious than succinylcholine.

The data indicate that such compounds have the capability of being useful as depolarizing muscle agents, and that certain of these compounds are more potent and efficacious than known muscle relaxants such as succinylcholine. The data also indicate that compounds of the present invention have the capability to activate human muscle receptors without activating ganglionic-type nicotinic acetylcholine receptors. The data show that the compounds of the present invention provide a therapeutic window for utilization as muscle relaxants. That is, at the levels that the compounds of the present invention are employed, those compounds show muscle relaxant effects to a significant degree but do not show undesirable peripheral effects to any significant degree. The data show that the compounds of the present invention beg/n to cause ganglionic effects only when employed in amounts of more than 15 time those required to begin to cause muscle relaxation.

What is claimed is:

1. The method for providing musculoskeletal relaxation in a patient undergoing a surgical procedure requiring anesthesia, the method comprising administering to the patient an effective amount of a compound having the formula:

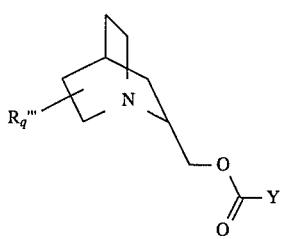

where R''' represents alkyl containing 1 to 7 carbon atoms or halo; q is an integer which ranges from 0–12; and Y is alkyl containing 1 to 7 carbon atoms.

2. The method of claim 1 whereby q is 0 or 1, and Y is methyl or ethyl.

3. The method of claim 1 whereby the compound is 2-acetoxymethylquinuclidine.

4. The method of claim 1 whereby the effective amount of the compound is at least about 0.001 mg/kg patient weight, but does not exceed about 0.5 mg/kg patient weight.

5. The method of claim 1 hereby the effective amount of compound is administered to the patient in an amount of at least about 0.00 1 mg/min./patient, but in an amount which does not exceed about 0.5 mg/min./patient.

6. A pharmaceutical composition having the form of a neuromuscular depolarizing muscle relaxant, the composition including as an active ingredient an effective amount of a compound having the formula:

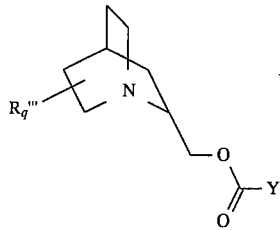

where R''' represents alkyl containing 1 to 7 carbon atoms or halo; q is an integer which ranges from 0–12; and Y is alkyl containing 1 to 7 carbon atoms.

7. The composition of claim 6 wherein q is 0 or 1, and Y is methyl or ethyl.

8. The composition of claim 6 wherein the compound is 2-acetoxymethylquinuclidine.

* * * * *